(12) United States Patent
Riener et al.

(10) Patent No.: US 7,241,145 B2
(45) Date of Patent: Jul. 10, 2007

(54) BIRTH SIMULATOR

(76) Inventors: Robert Riener, Werner-Egk-Strasse 18, 85591 Vaterstetten (DE); Rainer Burgkart, Pestalozzistrasse 27, 80469 Munchen (DE)

( * ) Notice: Subject to any disclaimer, the term of this patent is extended or adjusted under 35 U.S.C. 154(b) by 175 days.

(21) Appl. No.: 10/481,997

(22) PCT Filed: Jun. 25, 2002

(86) PCT No.: PCT/DE02/02338

§ 371 (c)(1),
(2), (4) Date: Aug. 30, 2004

(87) PCT Pub. No.: WO03/001482

PCT Pub. Date: Jan. 3, 2003

(65) Prior Publication Data

US 2005/0014115 A1 Jan. 20, 2005

(30) Foreign Application Priority Data

Jun. 25, 2001 (DE) .................. 101 30 485
Jan. 23, 2002 (DE) .................. 102 02 502
Jan. 23, 2002 (DE) .................. 102 02 503
Jan. 23, 2002 (DE) .................. 102 02 504

(51) Int. Cl.
*G09B 23/28* (2006.01)
(52) U.S. Cl. ..................................... 434/262
(58) Field of Classification Search .................. 434/262
See application file for complete search history.

(56) References Cited

U.S. PATENT DOCUMENTS

| 451,675 | A |  | 5/1891 | Klautsch |
| 3,822,486 | A | * | 7/1974 | Knapp et al. ............... 434/273 |
| 3,824,709 | A |  | 7/1974 | Knapp |
| 3,826,019 | A |  | 7/1974 | Knapp |
| 4,237,649 | A | * | 12/1980 | Goldfarb et al. ............ 446/330 |
| 4,411,629 | A |  | 10/1983 | Voights |
| 4,907,973 | A |  | 3/1990 | Hon |
| 5,509,810 | A | * | 4/1996 | Schertz et al. .............. 434/262 |
| 6,238,215 | B1 |  | 5/2001 | Jurmain et al. |
| 6,503,087 | B1 | * | 1/2003 | Eggert et al. ............... 434/262 |

FOREIGN PATENT DOCUMENTS

| WO | WO 02/01536 A1 | 1/2002 |
| WO | WO 02/29765 A1 | 4/2002 |

\* cited by examiner

*Primary Examiner*—Robert E. Pezzuto
*Assistant Examiner*—Cameron Saadat
(74) *Attorney, Agent, or Firm*—Kriegsman & Kriegsman

(57) ABSTRACT

The invention concerns an active and an interactive birth simulator for duplicating human pregnancy and the birth process, whereby the birth simulator has the following features: A womb torso 1, a child model 2, which is arranged in the womb torso 1, whereby natural shape, size and positional ratios are preferably maintained, and the child model 2 is connected to a controllable drive 5 via a coupling device 7, in order to move the child model 2 in the womb torso or to expel it from the womb torso 1 through the birth canal and a programmable control device is provided for controlling the drive 5.

7 Claims, 7 Drawing Sheets

1. movement animation
2. sound generator
3. movement data
4. birth simulation calculation
5. force-moment sensor
6. actuator (robot)
7. theoretical forces/moments
8. theoretical angle
9. motor currents
10. robotic control
11. integrated movement sensor mechanism
12. measured articulation angle
13. measured forces and moments Admittance control
"Robot reacts to force action by changing its trajectory"

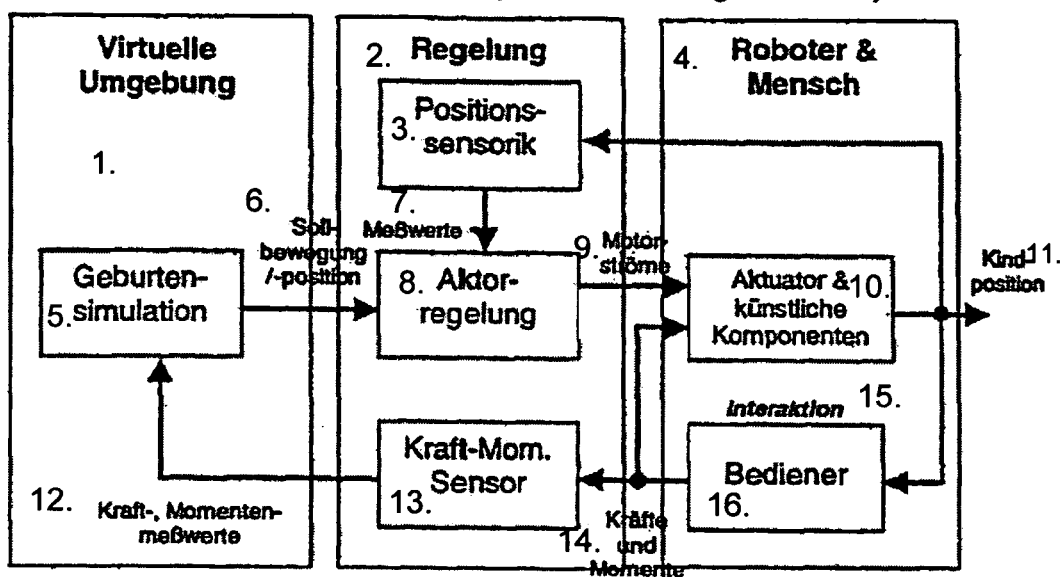

Fig. 10

1. Virtual environment
2. Control
3. Position sensor mechanism
4. Robot and human
5. Birth simulation
6. Theoretical movement/position
7. Measured values
8. Actuator control
9. Motor currents
10. Actuator and artificial components
11. Child position
12. Force, moment measured values
13. Force-moment sensor
14. Forces and moments
15. Interaction
16. Operator Impedance control
"Robot reacts to trajectory deviations by changing its force"

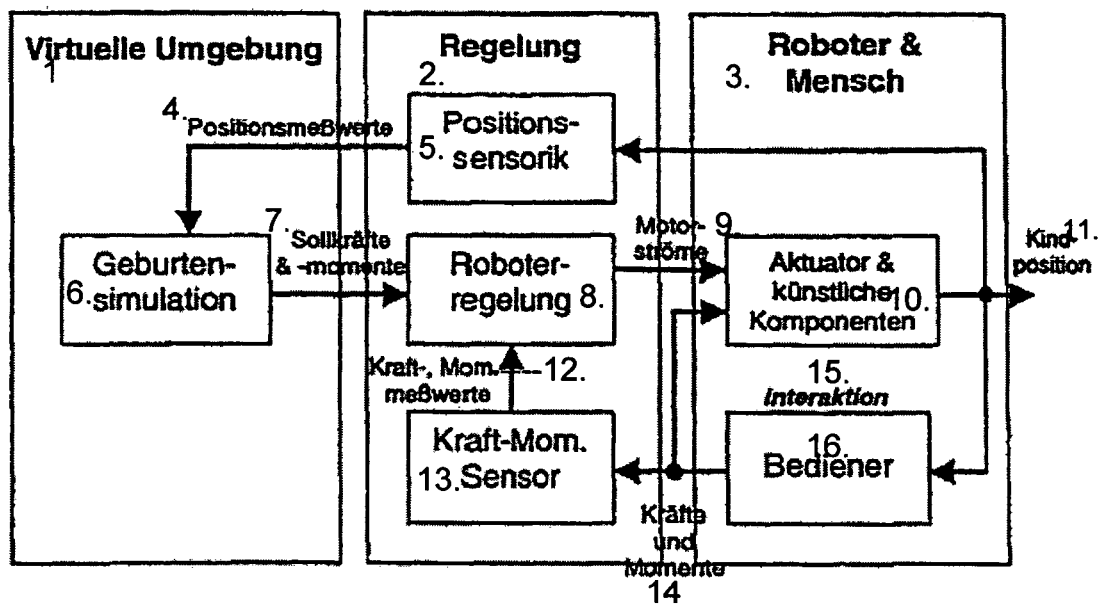

Fig. 11

1. Virtual environment
2. Control
3. Robot and human
4. Position measured values
5. Position sensor mechanism
6. Birth simulation
7. Theoretical forces and moments
8. Robotic control
9. Motor currents
10. Actuator and artificial components
11. Child position
12. Force, moment measured values
13. Force-moment sensor
14. Forces and moments
15. Interaction
16. Operator

BIRTH SIMULATOR

The invention concerns a birth simulator for duplicating prenatal treatment methods and for simulation of selected situations in the birth process.

The training of midwives and gynecologists is very expensive, since manual techniques to be practiced or the use of medical instruments (e.g., suction devices) can be undertaken only in a very limited way on pregnant women themselves, for various reasons. In complex emergency situations, it is neither possible nor ethically justifiable to actively include persons who are inexperienced in obstetrics. In addition, problem cases of wide variability are often not predictable. Thus, midwives and gynecologists must be present during births in a relatively passive manner over long time periods. Active training can commence only when passive training is very far advanced. All actions must then be supervised by experienced medical professionals in order to minimize any remaining risk to mother and child.

In order to support gynecological training, body models, films and computer animations have been used previously. These include hard plastic models which can be assembled and which make possible a spatial demonstration of anatomical, physiological or pathological interrelationships. Flexible models are also known, which will duplicate as well as possible human tactile properties, i.e., a deformable child-like doll is arranged in an anatomically correct uterus.

The midwives and gynecologists to be trained can thus take hold of these models and practice specific basic manual techniques and learn the spatial interrelationships, such as, e.g., the positions of the child.

Since the body models, films or computer animations which are known in the prior art, however, are insufficiently suitable for realistic training, the object of the invention is to create a device for duplicating prenatal treatment methods and for the simulation of selected situations in the birth process, so that the necessary manual techniques can be learned or trained basically more effectively. This device will still be designated below as a birth simulator.

This object will be solved with a birth simulator according to claim 1 and with a child model according to claim 8.

A womb torso preferably of flexible plastic or a material with comparable properties, which has the shape and hardness and thus the tactile feel of a natural human body, has a uterine cavity of a rubbery elastic material. The uterine cavity is shaped in such a way that a child model of flexible plastic can be introduced into it, whereby the uterine cavity and the child model correspond to natural relationships with respect to shape, size and position. According to the invention, the child model is mechanically coupled to a motor drive by means of a coupling device. In addition, a programmable control device is provided for controlling the mechanical drive, so that the child model can be moved in a freely programmable course of movement in the uterine cavity or can be delivered from the womb torso through the birth canal.

The advantage of the invention consists of the fact that a possibility has been created to simulate different medical situations, i.e., procedures prior to and during birth that evolve over time on a touchable and moving body model. The model can be touched with the hands, e.g., to feel how the child is expelled from the birth canal. It is also possible to practice the correct use of instruments, such as, e.g., the use of a forceps or a suction device. Of particular importance is the possibility of being able to set up another medical situation by changing the program, i.e., "by pushing a button".

According to claim 2, the child model is coupled with several controllable mechanical drives, so that complicated child movements can also be simulated, which correspond extensively to movements of a natural child. The different drives can also be preferably assembled in a multi-jointed robot.

According to claim 3, a sensor arrangement for detecting forces and movements and a simulation program for the simulation of force and movement feedback are also provided. When, e.g., a person making an exam presses the womb torso with his/her hands or touches the child model directly with his/her hands or grasps it with a medical instrument, the forces triggered thereby are measured by the sensors of the sensor arrangement. It is clear to the person skilled in the art that the directions of these forces can also be determined simultaneously directly or indirectly. The sensors are arranged on the coupling device and/or on the drive elements. The simulation program is implemented on the computer of the control device, which provides that the measured signals processed by the sensor arrangement are converted to force and motion feedback signals. These force and motion feedback signals are introduced into the control device, which regulates the drive elements in such a way that when the child model has been moved with a characteristic force effect by a person by means of the drive elements, adequate reaction movements are carried out by the child model, which correspond to the natural movement behavior of the child in the respective medical situation. The feel of a "living" child is communicated to the midwife or to the person being trained. Thus, for the first time, completely novel training methods are made possible in the field of maternity care and obstetrics. The most varied clinical situations and movement reaction patterns of the natural child can be simulated merely by changing the program, i.e., by pushing a button.

According to claim 4, an optical display device is additionally provided, which is connected to the computer of the control device via signal technology. This display device can be a monitor or data glasses. During a simulation, different visual information can be brought into play. When, e.g., a special situation of a birth is simulated, a film runs synchronously, which shows, e.g., the same situation as in a natural birth. However, other types of presentation can also be selected, such as, e.g., an x-ray film presentation.

According to claim 5, the optical display device also provides hints and additional information. It is particularly helpful for training, if, e.g., additional hints on dangerous situations are blended in.

According to claim 6, an acoustic generator is additionally provided for generating typical noises. Noises of the child as well as also articulations of the mother can be played in. The sounds can be generated synthetically or may also be of natural origin, i.e., they may involve tape recordings, which are recorded during an adequate natural situation. By this means, the person being trained is provided with a very realistic impression, if, e.g., in the case of vigorous contraction activity, at the same time, a groaning of the woman in labor is played in.

According to claim 7, the acoustic generators are integrated into the womb torso. In this way, the noises made by the child can be particularly genuinely simulated.

According to claim 8, a child model is provided, which is preferably designed for use in a birth simulator according to claims 1 to 7. The child model possesses distance and/or force and/or pressure sensors, which are connected to the computer of the control device via signal technology, in the neck region and/or in the region of the skull, which consists of deformable segments.

This child model makes it possible to improve the learning effect with the use of a birth simulator according to claims 1 to 7, so that additional information is obtained. Thus, e.g., the introductions of force on the child can be recorded while a trained person simulates a birth on the birth simulator. The person being trained will follow the same procedure. Then the two force curves can be compared and evaluated.

A preferred site for the application of a force and/or moment sensor is the neck of the child model. A preferred site for the application of distance sensors or pressure sensors is the skull region of the child model. When distance sensors are provided, the skull is deformable analogously to a natural child's skull and has movable skull segments, whose movements are measured by the distance sensors.

When the child model is used with a birth simulator according to claim 3, the sensor information of the child model can be used for providing more information as well as more accurate information on force and/or moments, for calculating the reaction forces and the reaction movements belonging thereto. It will be mentioned, in addition, that other sensors will also be arranged, if needed, by the person skilled in the art at suitable places on the child or also on the womb torso, when necessary for obtaining signals during the reproduction of a concrete movement simulation. Thus, pressure sensors can be arranged, e.g., on the abdominal region of the womb torso.

The invention will be explained in more detail below on the basis of examples of embodiment in conjunction with schematic drawings.

FIG. 10 shows a first control algorithm for an interactive embodiment of the invention.

FIG. 11 shows a second control algorithm for an interactive embodiment of the invention.

Figure 1:
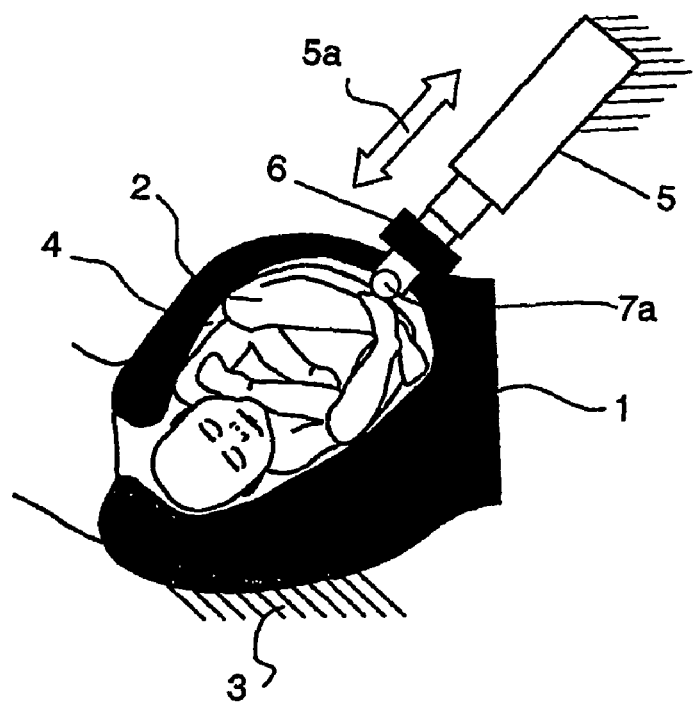
FIG. 1 shows a schematic representation of a first active embodiment of the invention.

FIG. 1 shows the cross section of a birth simulator in the size and shape of a womb torso 1 of a pregnant woman with a child model 2. The womb torso 1 is rigidly arranged in a region 3 on a support, e.g., a table. The child model 2 is found in a cavity 4, which simulates the uterus. The womb torso 1 and the child model 2 are made of a flexible plastic. A linear drive 5 is coupled to the child model 2 via a force sensor 6. The linear drive 5 has an internal position recognition device in the form of a length measurement system and makes possible a reciprocal movement in the directions of the arrow 5a. The force sensor 6 is connected with the child model 2 via a ball-and-socket joint 7a. When the linear drive 5 expels the child model 2 from the birth canal, a person being trained must hold and guide the child model 2 as in the case of an actual birth. The forces that act here are detected by the force sensor 6 and processed as measured force signals by an evaluating electronic device and stored in a storage device as measured force data. The force and movement patterns that can be followed in a simulated birth are compared with stored standard force and movement patterns. Conclusions on the success of training of the person being trained can be drawn from the deviations between the force and movement patterns which have been followed and the stored standard force and movement patterns.

Figure 2:
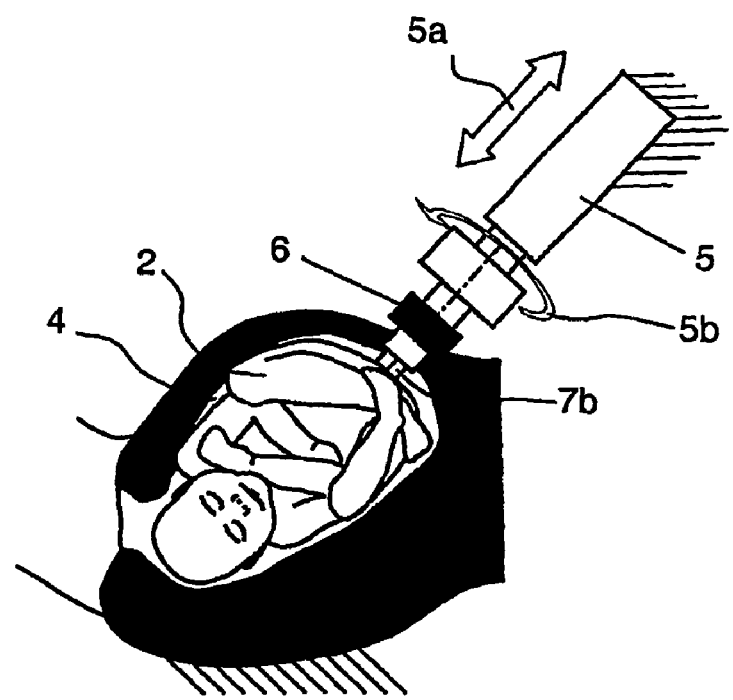
FIG. 2 shows a schematic representation of a second active embodiment of the invention.

FIG. 2 shows an arrangement that is basically identical to FIG. 1, wherein the linear drive 5, along with reciprocal movement 5a, additionally makes possible a rotational movement 5b. Unlike FIG. 1, the coupling site between the child model 2 and the force sensor 6 is shaped like a torsion-proof, spring elastic member 7b.

Figure 3:
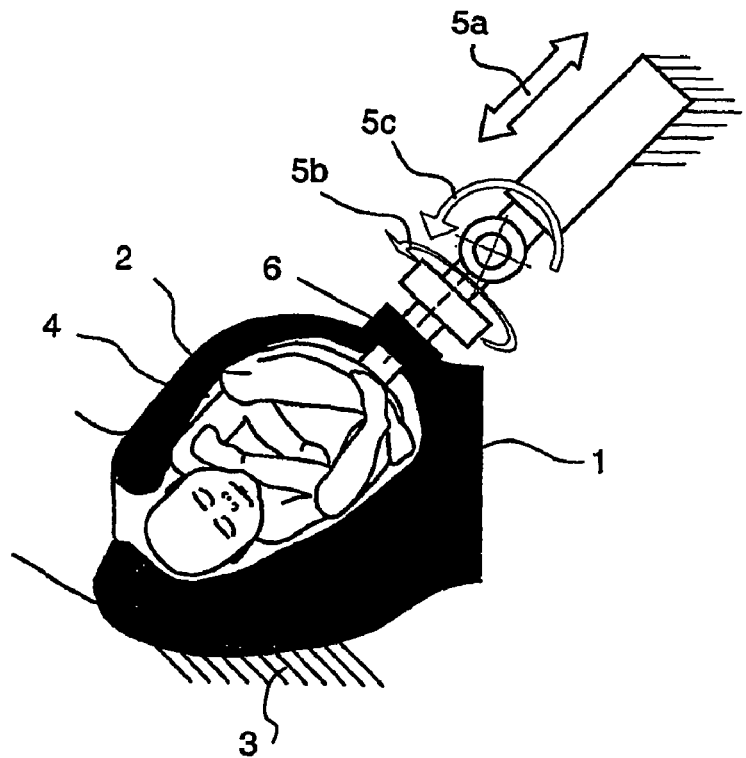
FIG. 3 shows a schematic representation of a third active embodiment of the invention.

FIG. 3 shows an arrangement that is basically identical to FIG. 2, wherein the linear drive 5, along with movements 5a and 5b, also makes possible a swinging movement 5c. Unlike FIG. 1 or 2, the coupling site between the child model 2 and the force sensor 6 is rigidly formed.

Figure 4:
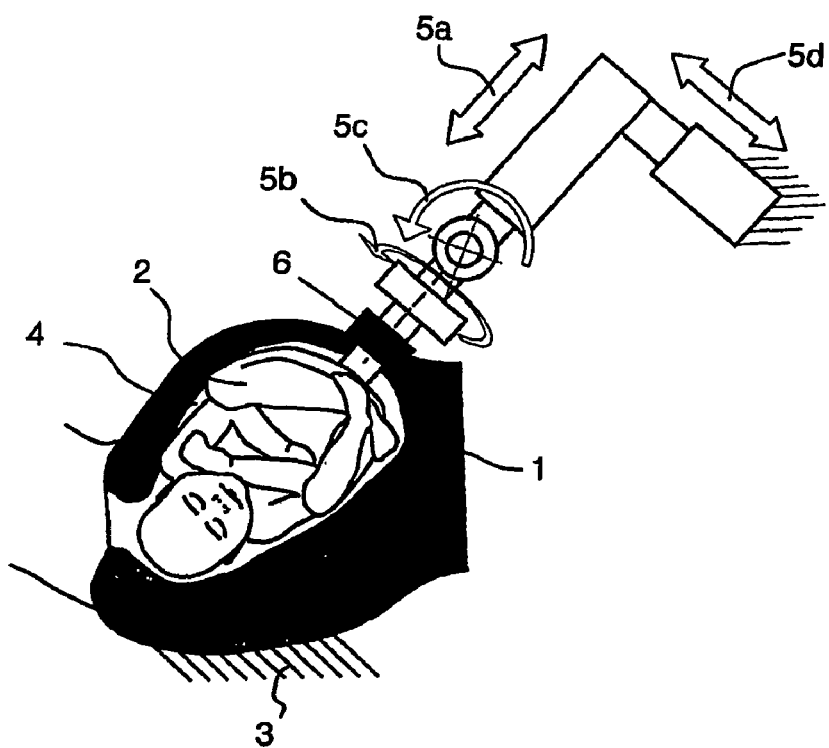
FIG. 4 shows a schematic representation of a fourth active embodiment of the invention.

FIG. 4 shows an arrangement that is basically identical to FIG. 3, wherein the linear drive 5, along with movements 5a, 5b and 5c conducts an additional movement 5d, which is at a right angle to the direction of movement 5a. The coupling site between the child model 2 and the force sensor 6 is also rigidly formed.

Figure 5:
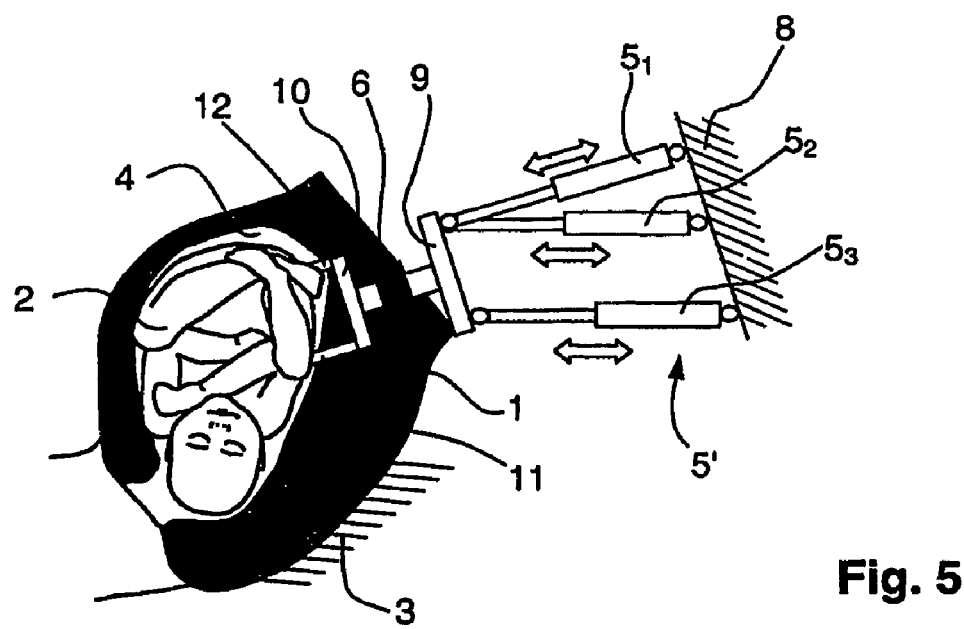
FIG. 5 shows a schematic representation of a fifth active embodiment of the invention.

FIG. 5 shows a linear drive 5, which consists of three individual drives $5_1$, $5_2$ and $5_3$, whose end segments can be tilted at an abutment 8 and are coupled to a plate 9. Plate 9 is rigidly connected to a two-point holder 10 via the force sensor 6. The two-point holder 10 fixes the child model 2 at points 11 and 12.

Figure 6:
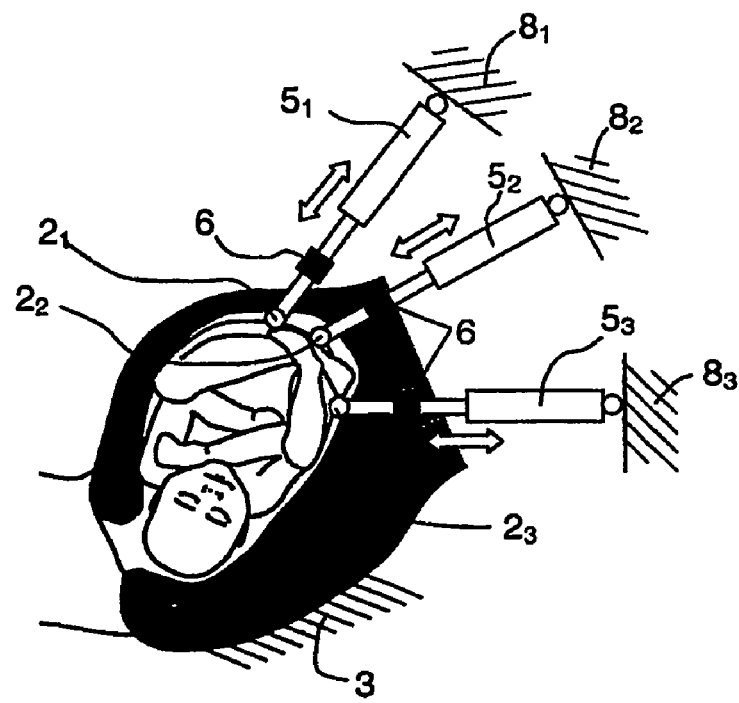
FIG. 6 shows a schematic representation of a sixth active embodiment of the invention.

FIG. 6 shows a linear drive 5, which, as described with reference to FIG. 5, also consists of three individual drives $5_1$, $5_2$ and $5_3$, whose end segments are coupled so that they each can be tilted at an abutment $8_1$, $8_2$ and $8_3$. The end segments extending in the direction of child model 2 are coupled so that they can be tilted at different points $2_1$, $2_2$ and $2_3$ on this latter.

Based on the schematic drawings and the above explanations, it is clear to the person skilled in the art as to how realistic movements of the child model can be effected by means of the different drives with different degrees of freedom.

Figure 7:
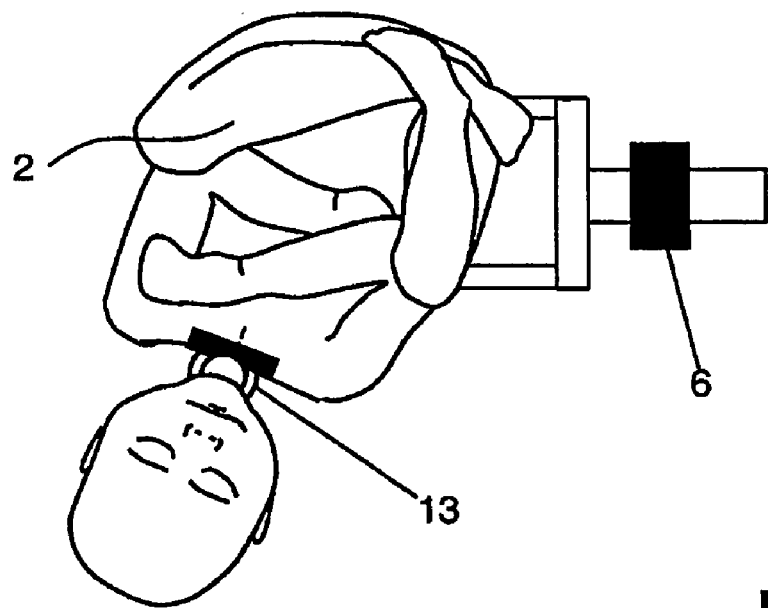
FIG. 7 shows a schematic representation of a first embodiment of a second invention.

FIG. 7 shows a child model 2, whose head is joined with the trunk via a force and moment sensor 13. It is particularly important for the birth simulation to practice manual techniques on the head of the child model 2. In this way, the neck of the child is particularly stressed. In monitoring a simulated birth, it is thus of particular importance to monitor the head manipulations, which is possible with this embodiment of a child model. Wired or wireless transfer methods can be used by the person skilled in the art for the transfer of measured electrical signals.

Figure 8:
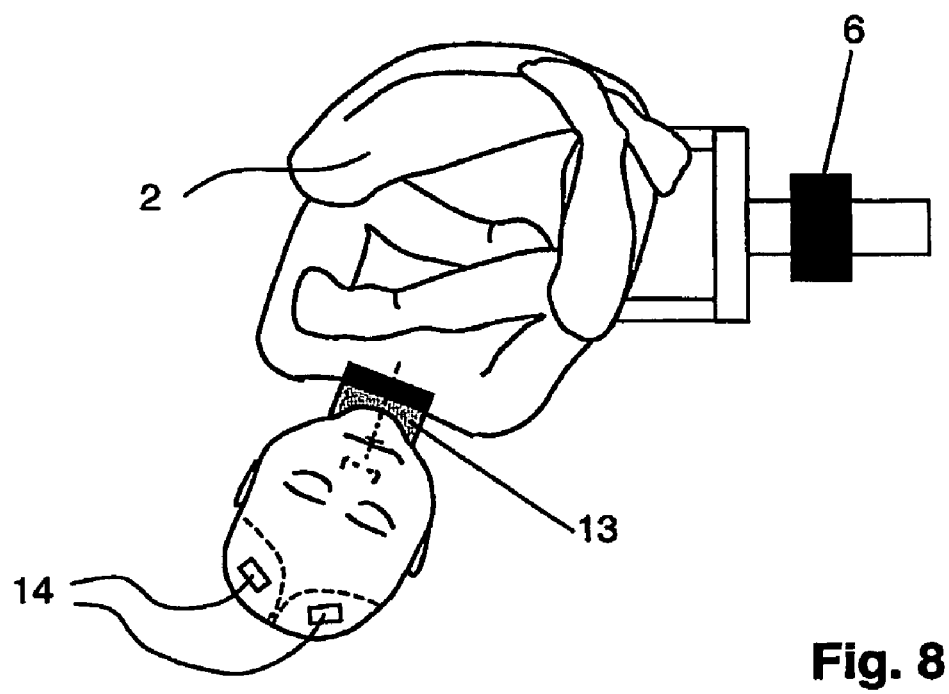
FIG. 8 shows a schematic representation of a second embodiment of a second invention.

FIG. 8 shows a child model 2, in contrast to the representation in FIG. 7, on whose head are arranged additional distance and pressure sensors 14 in the region of the skull bone. In addition, individual segments of the skull of the child model 2 are shaped so that they can be moved around. For example, if a birth is simulated, the segments of the skull move as they do in a natural birth process, whereby care is to be taken during training that such moves do not exceed medical limits given in advance. The displacements and pressures can be detected by means of the distance and pressure sensors during a simulated birth, and an evaluation can be made from the data obtained of whether the person being trained correctly holds and guides the head of the child model. The option is given to the person skilled in the art to select and to use suitable distance and pressure sensors and the signal processing technique suitable for this.

Figure 9:
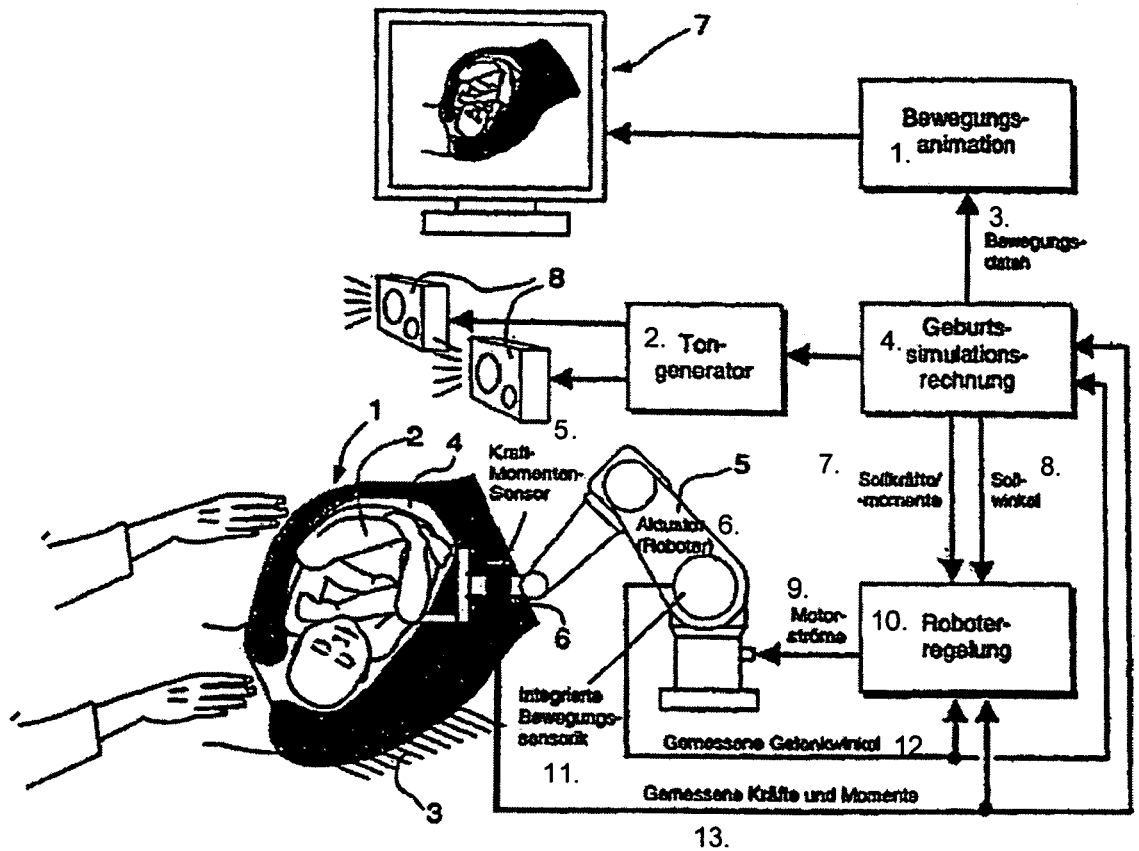
FIG. 9 shows an interactive embodiment of the invention.

FIG. 9 shows schematically the cross section of a birth simulator in the shape of an abdominal torso 1 of a pregnant woman with a child model 2. The abdominal torso 1 is rigidly arranged in a region 3 on a support, e.g., a table. The child model 2 is found in a cavity 4, which simulates the uterus. The abdominal torso 1 and the child model 2 are made of a flexible plastic. A robot 5 with 6 articulations is coupled to the child model 2 with serial kinematics via a six-component force-moment sensor 6.

When the robot 5 expels the child model 2 from the birth canal in a simulated birth, a person being trained must grasp and guide the child model 2, just like in a real birth. The forces and moments introduced thereby are detected by the six-component force-moment sensor 6, converted to electrical signals and introduced into a control and regulating device.

The robot has serial kinematics, i.e., several robotic segments are serially joined together via actively driven axes of rotation. The directions of the axes of rotation are selected such that the end effector of the robot can be moved in six degrees of freedom with the child model coupled to the six-component force-moment sensor 6 (three positions and three orientations). The angle positions of the robot are detected via internal articulated angle sensors and introduced into the control and regulating device. The position of child model 2 in space is determined from the articulated angle data.

If a person contacts the child model 2 with his hands indirectly via the flexible cover 6 of the structure or even directly, a movement is induced on the child model 2 by this person via the forces introduced by hand or by means of a medical instrument. The child model 2 reacts to this according to a movement pattern, which corresponds to the real reaction movement of a natural child. The induction of movement in the child model can be produced basically according to two methods:

The first method is the admittance control shown in FIG. 10, according to which the forces introduced by contact of the child model 2 are detected by the six-component force-moment sensor 6 and are transferred to the computer with the simulation program. There, the resulting movement of the child model 2 is calculated and passed on to the robotic control as a theoretical value. The robotic control compares the calculated theoretical movement with the measured robot movement and supplies the robot with motor currents, so that the error between measured and calculated movement is minimal.

The second method is the impedance control shown in FIG. 11, according to which the changes in position and orientation, which are forced by the effect of forces and moments, are detected and are passed on to the computer with the simulation program. After this, the corresponding forces and moments are calculated and passed on to the robotic control as theoretical values. The robotic control compares the calculated theoretical forces and moments with the actually occurring forces and moments and moves the robot so that the error that arises is minimal.

The simulation program for the birth simulator calculation thus includes a computer model, which contains the biomechanical relationships between pelvis, uterus, ligaments, tendons, skin and musculature of the mother and the body of the child model. It describes the static and dynamic interrelationships between the forces and moments that occur, which a person, such as, e.g., the midwife in training, introduces onto the child model, and the positions and movements of the child relative to the spatial positions/ orientations and their derivatives, i.e., velocities and accelerations relative to the body of the mother. In this way, either the resulting movements of the child model 2 can be calculated from the measured forces and moments (admittance control) or from the measured child movement, the forces and moments that belong thereto which are transferred to the person who performs the actions, can be calculated (impedance control).

By regulating the mechanical force actuator 5, the person who performs the actions has the tactilely subjective impression of a real reaction; Not only normal birth processes or child movements can be simulated by appropriate selection of parameters in the birth simulator calculation, but also rare situations and problem cases can be represented and visually communicated.

In the embodiment of the invention according to FIG. 9, the movements and deformations of the anatomical components, such as, e.g., pelvis, uterus, ligaments, tendons, skin, musculature of the mother and of the child, are also determined in a movement animation calculation from the movement information which is processed in the birth simulation, and are visualized in real time on a monitor 7. Different types of presentation can be selected, such as, e.g., the x-ray-like presentation that is shown or an ultrasound-like presentation, wherein, e.g., particularly endangered segments or lesions can be emphasized by colors. It is also possible to switch between different types of presentation. Since the visual information is transmitted simultaneously with the tactile information to the person who performs the actions, a very realistic total impression is formed for this person.

In the embodiment of the invention according to FIG. 9, pain threshold values are also determined from the biomechanical calculations and when these values are exceeded, a command is triggered for playing back a sound program. These sound programs are filed in a memory and are called up on request and reproduced over a stereo speaker system 8. It is of lasting psychological learning effect for the person who performs the actions, if, e.g., a loud sound of pain is emitted when an incorrect manipulation is made.

Further suggestions for producing the actuator and its control will be given below.

The actuator was verified by means of a six-axis Stäubli industrial robot RX90. The original control computer of the robot requires relatively long cycle times of more than 16 ms. For a stable operation of the birth simulator and a disturbance-free, realistic presentation of biomechanical properties, under certain circumstances, higher scanning rates in the kHz range under real-time conditions and a high computing power are necessary for implementing the model-based control process. For this reason, a PC-based control was constructed in parallel. The angle, force, and moment sensors and the analog signals for the electronic articulation amplifier of the Stäubli computer can be switched via a reversing switch to the PC, where signals can be captured or output via the corresponding PC interface cards. The above-described control based on articulated moment interfaces can thus be implemented on the PC by configuration of the electronic articulation amplifier to a current control. Due to the essentially higher computing power of the PC, the scanning time can thus be shortened to 250 µs, which leads to substantially better results than with the original architecture. Of advantage in this procedure is the fact that all original components such as the articulation amplifier, the safety electronics for brakes and the emergency stop circuit as well as the power supply remain and can also be used.

Further suggestions for producing the biomechanical model will be given below.

For implementing the invention, a basic biomechanical model must be developed. The relationship between the loads impressed on the child from outside (operator), i.e., forces and moments (cause) and the basic movement or position (effect) is represented in the biomechanical model. Although the cause-effect or effect-cause principle is described now for mathematical representation, it depends on the type of control. An inverse model is required for the admittance control, i.e., the causes (forces, moments) are calculated as a function of effects (positions, velocities). And vice versa, effects are calculated from causes in the impedance control in a direct dynamic model (also named the forward model). The mode of calculation, i.e., whether inverse or direct, is only of subordinate importance for the modeling. An example of modeling in the direct mode is outlined in the following:

The child possesses a specific anatomically conditioned shape/geometry, which can be considered rigid and stiff in the simplest case. However, is is logically assumed that the shape of the child is passively viscoelastically deformed by forces which are exercised on the child by the operator or by contact with segments of the womb. Likewise, the womb [torso], consisting of uterus, abdomen, birth canal, pelvis, etc., possesses specific geometric and viscoelastic properties.

Now when a force and/or a moment is exercised on the child by the operator, these loads are transferred via the child to the child-mother contact sites (e.g., in the uterus or in the birth canal). Relative movements caused by deformation and friction occur at these sites. Depending now on how the geometric and viscoelastic properties of the corresponding (i.e., involved) body segments of the mother and child are configured, movements occur with varying degree of clarity (clearly means here: rapid or to a notable extent). The position of the child can thus be influenced by the introduction of loads from outside (via the vagina or abdominal wall). It should be noted that the child can move out of the womb even without outside interference—just by the contraction of the uterus, as long as great mechanical or muscular resistance does not occur. However, if a narrowing of the birth canal is present or the skull of the child "tilts" due to an unfavorable oblique position in the birth canal, then the operator must introduce forces and moments so that he/she either increases the "expelling forces" (e.g., by downward pressure on the abdominal wall of the mother) or eliminates the tilting by rotational movements of the child's head (by grasping it from the outside in the birth canal).

The biomechanical model need not necessarily explicitly include all anatomical components and shapes. A certain "abstracted" representation of the mathematical relationships between impressed forces and resulting movements is achieved. That is, a mathematical function describes which position, orientation and velocity result when a force and a moment act in a certain direction at a specific site on the child. In this way, the multidimensional nature of the problem can be taken care of. That is, the forces and moments that are introduced act in 3D directions and can attack at any site on the surface of the child. The resulting positions, orientations and velocities are likewise to be indicated in 3D. The relationship between force/moment and position/movement also still depends on the instantaneous position of the child in the uterus or in the birth canal. These mathematical relationships can be easily described on the basis of linear or nonlinear algebraic equations. Formulating the correct parameters, however, is difficult. The selection of parameters determines how close to reality a normal or pathological birth process can be simulated. The parameters can be estimated on the basis of theoretical considerations or can be obtained experimentally by measurement technology.

Further suggestions for producing the graphic display will be given below. Internal anatomical components, such as pelvic bone, uterus, placenta, uterine orifice, blood vessels, as well as the child are visualized with a monitor. Optionally the monitor can be operated in stereo mode together with shutter glasses. The movement animation is produced synchronously with the movements of the birth simulator. In this way, it is possible for the operator to study the anatomical and biomechanical relationships inside the body even when the child is moving. Visualization is produced on the basis of segmented and 3D-reconstructed CT and MRT images. The reconstructed anatomical presentation represents additional information, which has high didactic value in medical training, but cannot be made visible in a real birth. Usually in the clinical routine, only ultrasound techniques are used for observation and evaluation of the birth. Such ultrasound images can be simulated in the movement animation on the basis of assembled individual images that run synchronously with the birth.

In the graphic animation, movement-synchronous changes in position of body segments, changes in the course of blood vessels or umbilical cord, as well as deformations of muscles, uterus, placenta, etc. are taken into consideration. A visualization of such movement processes is possible due to so-called "cinematic CT and MRT images". This involves, however, only a cinematographic technique, which does not permit interactive operation in more than one degree of freedom and thus is suitable for application in the VR [visual reality] field only to a limited extent (Dupuy et al. 1997; Witonski and Goraj 1999). A model-based animation represents an alternative. All components are modeled therein in their relevant geometric and viscoelastic properties and their mechanical interplay. For a realistic simulation, however, front-end calculations and complex multi-unit contact models are required, which considerably increase the expenditure for simulation technology and can endanger the real-time capability of the system.

Therefore, a combined method is recommended, in which image data as well as anatomical model considerations are used. This approach consists of interpolating and extrapolating geometric data, which are reconstructed from numerous discrete birth moments, in such a way that any arbitrary position of the child can be represented in any important degree of freedom. The interpolation and extrapolation can be produced, supported by the model, by taking into consideration, for example, the volume retention or length constancy of specific body segments. Since this is possible with relatively small calculation expense, smooth movement courses that can be performed in real time can be obtained in any arbitrary direction.

Further suggestions for producing the acoustic display will be given below. A number of different acoustic signals occur during birth, which can be generated on the speakers. These include cries of pain from the mother, sounds when the child is expelled, acoustically represented signals, such as, e.g., contraction activity of the mother and the EKG of the child. The speakers can be placed in the vicinity of the synthetic body segments or incorporated in the body segments so that they are not visible from the outside.

The birth sounds can be taken from several subjects during birth. Models must be found to present the sounds, which interrelate the type of noise with the situation that is the basis for it and the movement actions carried out by the operator. These interrelationships can be described first qualitatively with the help of linguistic variables, based on the experience of a number of gynecologists. Then quantitative interrelationships can be derived from the linguistic data by the method of fuzzy logic.

The invention claimed is:

1. A birth simulator with the following features:
a womb torso of flexible material,
a child model of flexible material, which is arranged in the womb torso, wherein natural shape and size ratios and haptics are preferably maintained, the child model is connected to a controllable drive via
a coupling device in order to move the child model in the womb torso or expel it from the womb torso through a birth canal, and
a programmable control device for controlling the drive, which comprises a computer is provided, is hereby characterized in that
a sensor arrangement is provided for detecting forces and movements exerted onto the womb torso or the child model by an examining individual using the hands or medical instruments, wherein sensors of the sensor arrangement are fixed on the coupling device and/or the controllable drive and
the control device comprises
an admittance control or
an impedance control for controlling the drive elements, wherein the control device is configured so that measured signals supplied by the sensor arrangement are sent to the computer, in which
a simulation program is stored, which, when an exercising individual exerts external forces onto the child model, co-operates with the admittance control or the impedance control of the control device to cause the controllable drive to move the child model so that its movements correspond to the natural movement behavior of a child in its mother's womb during a certain examination or a certain phase of birth.

2. The birth simulator according to claim 1, further characterized in that several coupling devices and several controllable drives are provided for the movement of the child model.

3. The birth simulator according to claim 1, further characterized in that an optic display device connected by signal technology to the control device is provided, which shows the movements of the child in real time.

4. The birth simulator according to claim 3, further characterized in that the optic display device indicates hints and additional information.

5. The birth simulator according to claim 1, further characterized in that an acoustic generator connected by signal technology to the control device is provided for the generation of typical noises and articulations, which can occur during real examinations or during natural birth.

6. The birth simulator according to claim 5, further characterized in that the acoustic generators are integrated in the womb torso.

7. A child model, preferably for a birth simulator according to any one of claims 1–6, further characterized in that distance and/or force and/or pressure sensors, which are connected to the control device via signal technology, are arranged on the child model in the neck region and/or in the region of the skull, which consists of deformable segments.

* * * * *